United States Patent [19]
McKay

[11] Patent Number: 6,039,762
[45] Date of Patent: *Mar. 21, 2000

[54] REINFORCED BONE GRAFT SUBSTITUTES

[75] Inventor: William F. McKay, Memphis, Tenn.

[73] Assignee: SDGI Holdings, Inc., Wilmington, Del.

[ * ] Notice: This patent is subject to a terminal disclaimer.

[21] Appl. No.: 08/872,689

[22] Filed: Jun. 11, 1997

Related U.S. Application Data

[63] Continuation-in-part of application No. 08/485,842, Jun. 7, 1995, Pat. No. 5,702,449.

[51] Int. Cl.[7] ........................................................ A61F 2/44
[52] U.S. Cl. ................................. 623/17; 623/16; 606/60; 606/61
[58] Field of Search ........................... 623/16, 17; 606/60, 606/61

[56] References Cited

U.S. PATENT DOCUMENTS

| | | | |
|---|---|---|---|
| 4,309,488 | 1/1982 | Heide et al. | 428/547 |
| 4,599,086 | 7/1986 | Doty | 623/17 |
| 4,626,392 | 12/1986 | Kondo et al. | 264/62 |
| 4,636,217 | 1/1987 | Ogilvie et al. | 623/17 |
| 4,654,314 | 3/1987 | Takagi et al. | 501/82 |

(List continued on next page.)

OTHER PUBLICATIONS

Anterior Cervical Discectomy and Vertebral Interbody Fusion with Hydroxy–Apatite Ceramic. Preliminary Results., D. K. Boker, R. Schultheib, D. van Roose, B. Kaden; Acta Neurochirurgica, Spring 1993.

Osteogenesis by Subcutaneous Implantation of Calcium Phosphates—A Histological Description, J. M. Toth, K. L. Lynch, and D. A. Hackbarth, 39th Annual Meeting, Orthopaedic Research Society, Feb. 15–18, 1993.

The Influence of Multiphase Calcium Phosphate Bioceramics on Bone Formation in Nonosseous Tissues, Li. Yubao, Zhang Xingdong, Chen Weiqun, Liu Yuhua, 19th Annual Meeting of the Society for Biomaterials, Apr. 28–May 2, 1993.

Osteoinductivity by Subcutaneous Implantation of a Fibrillar Collagen and a Calcium Phosphate Ceramic Composite, K. L. Lynch, J. M. Toth, K. R. Hamson, K. C. Ho, W. M. Hirthe, Presented Nov., 1990.

Ceramic Anterior Spinal Fusion: Biological and Biomechanical Comparison in a Canine Model, S. e. Emery, D. A. Fuller, J. S. Bensusan, S. Stevenson, 40th Annual Meeting, Orthopaedic Research Society, Feb. 21–24, 1994.

Osteoinductivity by Calcium Phosphate Ceramics, J. M. Toth, K. L. Lynch and K. R. Hamson, Fourth World Biomaterials Congress, Apr. 24–28, 1992.

Evaluation of Collagen/Ceramic Bone Graft Substitutes With Osteoinductive Composites in Dogs with Segmental Spinal Instrumentation, T. J. Flatley, K. L. Lynch, D. A. Ladwig, D. A. Skrade, Papers #74, Milwaukee, WI.

(List continued on next page.)

Primary Examiner—Paul B. Prebilic
Attorney, Agent, or Firm—Woodard, Emhardt, Naughton Moriarty & McNett

[57] ABSTRACT

One embodiment of a spinal spacer 10 includes a body 11 sized and configured for engagement between adjacent vertebrae V. The body 11 includes two opposite faces 12, 14 and an outer surface 13 between the two faces 12, 14. In one embodiment, the body 11 includes deactivated bone material in synergistic combination with a bone growth factor. A sleeve 15 is disposed around the outer surface 13 of the body 11. The sleeve 15 is composed of a second material which is relatively stronger under compressive loads than the biocompatible material of the body 11. Also provided is a plurality of apertures 16 through the sleeve 15 in communication with the outer surface 13 of the body 11 for bone ingrowth. Means for attaching the sleeve to the endplates of adjoining vertebral bodies are also provided.

36 Claims, 6 Drawing Sheets

U.S. PATENT DOCUMENTS

| | | | |
|---|---|---|---|
| 4,687,675 | 8/1987 | Nakano et al. | 427/2 |
| 4,714,469 | 12/1987 | Kenna | 623/17 |
| 4,722,870 | 2/1988 | White | 428/621 |
| 4,820,305 | 4/1989 | Harms et al. | 623/16 |
| 4,834,757 | 5/1989 | Brantigan | 623/17 |
| 4,878,915 | 11/1989 | Brantigan | 623/17 |
| 4,917,703 | 4/1990 | Albrektsson | 623/66 |
| 4,961,740 | 10/1990 | Ray et al. | 606/61 |
| 4,976,738 | 12/1990 | Frey et al. | 623/16 |
| 5,002,583 | 3/1991 | Pitaru et al. | 623/66 |
| 5,015,247 | 5/1991 | Michelson | 606/61 |
| 5,026,373 | 6/1991 | Ray et al. | 606/61 |
| 5,055,104 | 10/1991 | Ray | 606/61 |
| 5,147,402 | 9/1992 | Bohler et al. | 623/16 |
| 5,152,791 | 10/1992 | Hakamatsuka et al. | 623/16 |
| 5,219,363 | 6/1993 | Croninshield et al. | 623/23 |
| 5,282,861 | 2/1994 | Kaplan | 623/16 |
| 5,306,302 | 4/1994 | Bauer et al. | 623/16 |
| 5,306,303 | 4/1994 | Lynch | 623/16 |
| 5,306,307 | 4/1994 | Senter et al. | 623/17 |
| 5,330,826 | 7/1994 | Taylor et al. | 428/216 |
| 5,346,492 | 9/1994 | Morgan | 606/60 |
| 5,443,515 | 8/1995 | Cohen et al. | 623/17 |
| 5,514,180 | 5/1996 | Heggeness et al. | 623/17 |
| 5,702,449 | 12/1997 | McKay | 623/17 |
| 5,755,798 | 5/1998 | Papavero et al. | 623/17 |
| 5,776,199 | 7/1998 | Michelson | 606/61 |
| 5,782,919 | 7/1998 | Zdeblick et al. | 623/17 |
| 5,865,845 | 2/1999 | Thalgott | 623/17 |
| 5,888,224 | 3/1999 | Beckers et al. | 623/17 |

OTHER PUBLICATIONS

Macroporous Biphasic Calcium Phosphate as a Bone Substitute for Postero–Lateral Spine Fusion. Biomechanical Evaluation in Sheep. P. Guigui, P. Y. Plais, D. Chopin, F. Lavaste, P. Hardouin, ISSLS Jun. 15–19, 1993.

Biphasic Calcium Phosphate as a Bone Graft Substitute for Spine Fusion: Stiffness Evaluation, J. Delecrin, N. Passuti, J. Royer, G. Daculsi and Y. Maugars, Fourth World Biomaterials Congress, Apr. 24–28, 1992.

Comparison of Compressive Strengths of Iliac Bone Grafts and Porous Calcium Phosphate Ceramics for Spinal Fusion, J. M. Toth, T. H. Lim, H. S. An, R. Xu, Y. Ran, and L. M. McGrady, 40th Annual Meeting, Orthopaedic Research Society, Feb. 21–24, 1994.

Ceramic–Induced Osteogenesis Following Subcutaneous Implantation of Calcium Phosphates, J. M. Toth, K.L. Lynch and D. A. Hackbarth, Bioceramics, vol. 6, Nov. 1993.

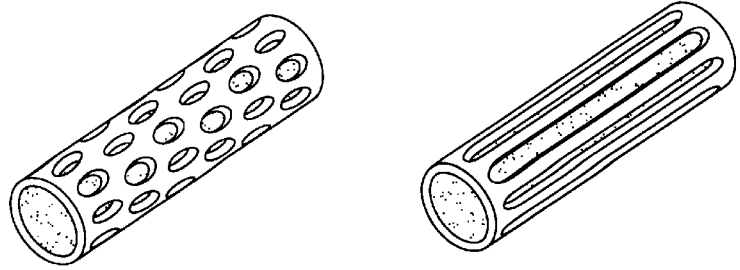
Fig. 6    Fig. 7
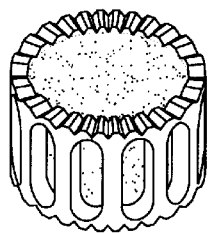 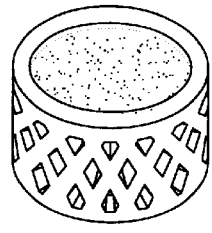
Fig. 8    Fig. 9    Fig. 10
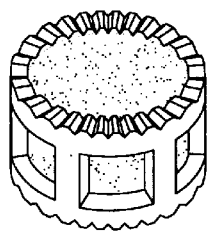 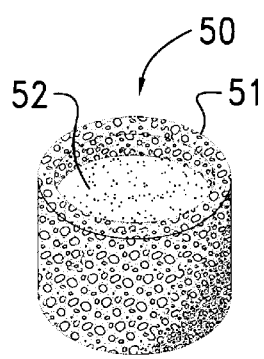 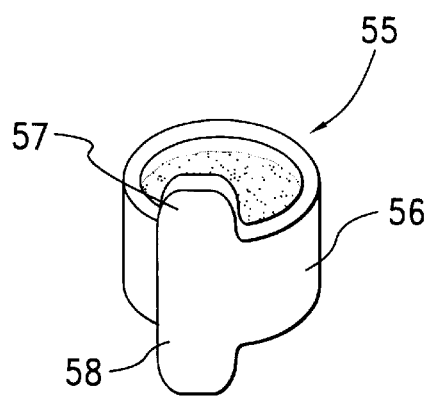
Fig. 11    Fig. 12    Fig. 13

REINFORCED BONE GRAFT SUBSTITUTES

The present invention is a continuation-in-part of Ser. No. 08/485,842, filed Jun. 7, 1995, now U.S. Pat. No. 5,702,449, issued Dec. 30, 1997, entitled REINFORCED POROUS SPINAL IMPLANTS.

FIELD OF THE INVENTION

The present invention broadly concerns stabilizing the spine. Specifically, the invention concerns a reinforced bone graft substitute.

BACKGROUND OF THE INVENTION

Intervertebral discs, located between the endplates of adjacent vertebrae, stabilize the spine, distribute forces between vertebrae and cushion vertebral bodies. A normal intervertebral disc includes a semi-gelatinous component, the nucleus pulposus, which is surrounded and confined by an outer, fibrous ring called the annulus fibrosus. In a healthy, undamaged spine, the annulus fibrosus prevents the nucleus pulposus from protruding outside the disc space.

Spinal discs may be displaced or damaged due to trauma, disease or aging. Disruption of the annulus fibrosus allows the nucleus pulposus to protrude into the vertebral canal, a condition commonly referred to as a herniated or ruptured disc. The extruded nucleus pulposus may press on the spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain.

Sometimes the only relief from the symptoms of these conditions is a discectomy, or surgical removal of a portion or all of an intervertebral disc followed by fusions of the adjacent vertebrae. The removal of the damaged or unhealthy disc will allow the disc space to collapse. Collapse of the disc space can cause instability of the spine, abnormal joint mechanics, premature development of arthritis or nerve damage, in addition to severe pain. Prosthetic implants are often used to prevent collapse of the space. The implant must provide temporary support and allow bone ingrowth. Success of the discectomy and fusion procedure requires the development of a contiguous growth of bone to create a solid mass because the implant may not withstand the compressive loads on the spine for the life of the patient.

Many attempts to restore the intervertebral disc space after removal of the disc have relied on metal devices. U.S. Pat. No. 4,878,915 to Brantigan teaches a solid metal plug. U.S. Pat. Nos. 5,044,104; 5,026,373 and 4,961,740 to Ray; U.S. Pat. No. 5,015,247 to Michelson and U.S. Pat. No. 4,820,305 to Harms et al. teach hollow metal cage structures. There are several disadvantages associated with the use of these metal implants. Solid body metal implants do not allow bone ingrowth which may lead to the eventual failure of the implant. Surface porosity in such solid implants does not correct this problem because it will not allow sufficient ingrowth to provide a solid bone mass strong enough to withstand the loads of the spine. On the other hand, the hollow cage structures of Harms, Ray and Michelson allow ingrowth. These devices can also be filled with bone graft material to promote bone growth. Unfortunately, many of these devices are difficult to machine and therefore expensive. Furthermore, metal implants may stress shield the bone graft, increasing the time required for fusion to occur.

The Michelson implant further requires a special tool and additional preparation of the adjacent vertebral bodies to ensure fusion. A special press is required to forcibly inject a compressed core of osteogenic material into the device. The osteogenic material, which is removed from the patient's iliac crest, must be compressed so that the graft material extends through openings in the implant whereby the graft material directly contacts the bone of the adjacent vertebral bodies. Michelson also requires coring out an area of each adjacent vertebral body to provide sufficient surface area of contact between the implant and the cortical bone of the vertebrae.

The use of bone graft materials in these past metal cage fusion devices presents several disadvantages. Autografts, bone material surgically removed from the patient, are undesirable because they may not yield a sufficient quantity of graft material. The additional surgery to extract the autograft also increases the risk of infection and may reduce structural integrity at the donor site. The supply of allograft material, which is obtained from donors of the same species, is not limited. However, allografts are also disadvantageous because of the risk of disease transmission and immune reactions. Furthermore, allogenic bone does not have the osteogenic potential of autogenous bone and therefore will give only temporary support.

Due to the need for safer bone graft materials, bone graft substitutes, such as bioceramics have recently received considerable attention. Calcium phosphate ceramics are biocompatible and do not present the infectious or immunological concerns of allograft materials. Ceramics may be prepared in any quantity which is a great advantage over autograft bone graft material. Furthermore, bioceramics are osteoconductive, stimulating osteogenesis in boney sites, and are also thought to be osteogenic, able to initiate osteogenesis in non-boney sites. Bioceramics provide a porous matrix which further encourages new bone growth. Unfortunately, ceramic implants lack the strength to support high spinal loads and therefore require separate fixation before the fusion.

Of the calcium phosphate ceramics, hydroxyapatite and tricalcium phosphate ceramics have been most commonly used for bone grafting. Hydroxyapatite is chemically similar to inorganic bone substance and biocompatible with bone. However, it is slowly degraded. β-tricalcium phosphate is rapidly degraded in vivo and is too weak to provide any support. These ceramics have proven unsatisfactory for providing temporary support after discectomy while awaiting fusion.

A need has remained for fusion spacers which stimulate bone ingrowth and avoid the disadvantages of metal implants yet provide sufficient strength to support the vertebral column until the adjacent vertebrae are fused.

A need has also remained for bone graft substitutes which provide the osteogenic potential and low risk of infectious or immunogenic complications of allograft without the disadvantages of autograft.

SUMMARY OF THE INVENTION

In accordance with the invention, a spinal spacer is provided for engagement between vertebrae. The spacer includes a body sized and configured to fill the space between the vertebrae and having two opposite faces and an outer surface between the two faces. The body includes a porous biocompatible material for permitting tissue ingrowth therethrough. In some embodiments the material is a bioceramic or a bone material. A sleeve is disposed around the outer surface of the body. The sleeve is composed of a second material which is relatively more rigid than the biocompatible material of the body. The invention also contemplates an interbody fusion spacer having a height approximating the height of a human disc space. In another specific embodiment, a vertebral body replacement spacer is provided for restoring the space left by the removal of a defective spinal element located between adjoining healthy vertebral bodies.

In one specific embodiment of the invention, there is provided a plurality of apertures through the sleeve in communication with the outer surface of the body for bone ingrowth. In another embodiment, the sleeve is formed of a temperature responsive material such that the chamber has a first inner dimension that is slightly larger than an outer dimension of the body when the sleeve is in a heated state to slidably receive the body within the sleeve. The chamber has a second inner dimension that is slightly smaller than the body when the sleeve is in a cooled state to thereby clamp the body therein.

In another specific embodiment of the invention, there is provided attaching means for attaching the sleeve to the endplates of adjoining vertebral bodies.

One object of the invention is to provide a spacer for engagement between vertebrae which encourages bone ingrowth and avoids stress shielding. Another object of the invention is to provide a spacer which restores the intervertebral disc space and supports the vertebral column while promoting bone ingrowth. A further object is to provide a vertebral body replacement spacer for use in restoring the space left by the removal of a defective spinal element while promoting fusion between the adjoining healthy vertebral bodies.

In one aspect, the invention provides a deactivated bone graft in synergistic combination with a bone growth factor and reinforced with a sleeve. This embodiment is advantageous because it combines the natural mineral structure of bone with the osteoinductive power of a bone growth protein in a load bearing spacer.

One benefit of the spacers of the present invention is that they combine the advantages of porous, biocompatible materials such as ceramics and bone products with the advantages of metals, without the corresponding disadvantages of each material. An additional benefit is that the invention provides a stable scaffold for bone ingrowth before fusion occurs. Other objects and further benefits of the present invention will become apparent to persons of ordinary skill in the art from the following written description and accompanying Figures.

BRIEF DESCRIPTION OF THE DRAWINGS

FIGS. 5–13 are alternate embodiments of the implant of FIG. 1.

DESCRIPTION OF THE PREFERRED EMBODIMENTS

Figure 1:
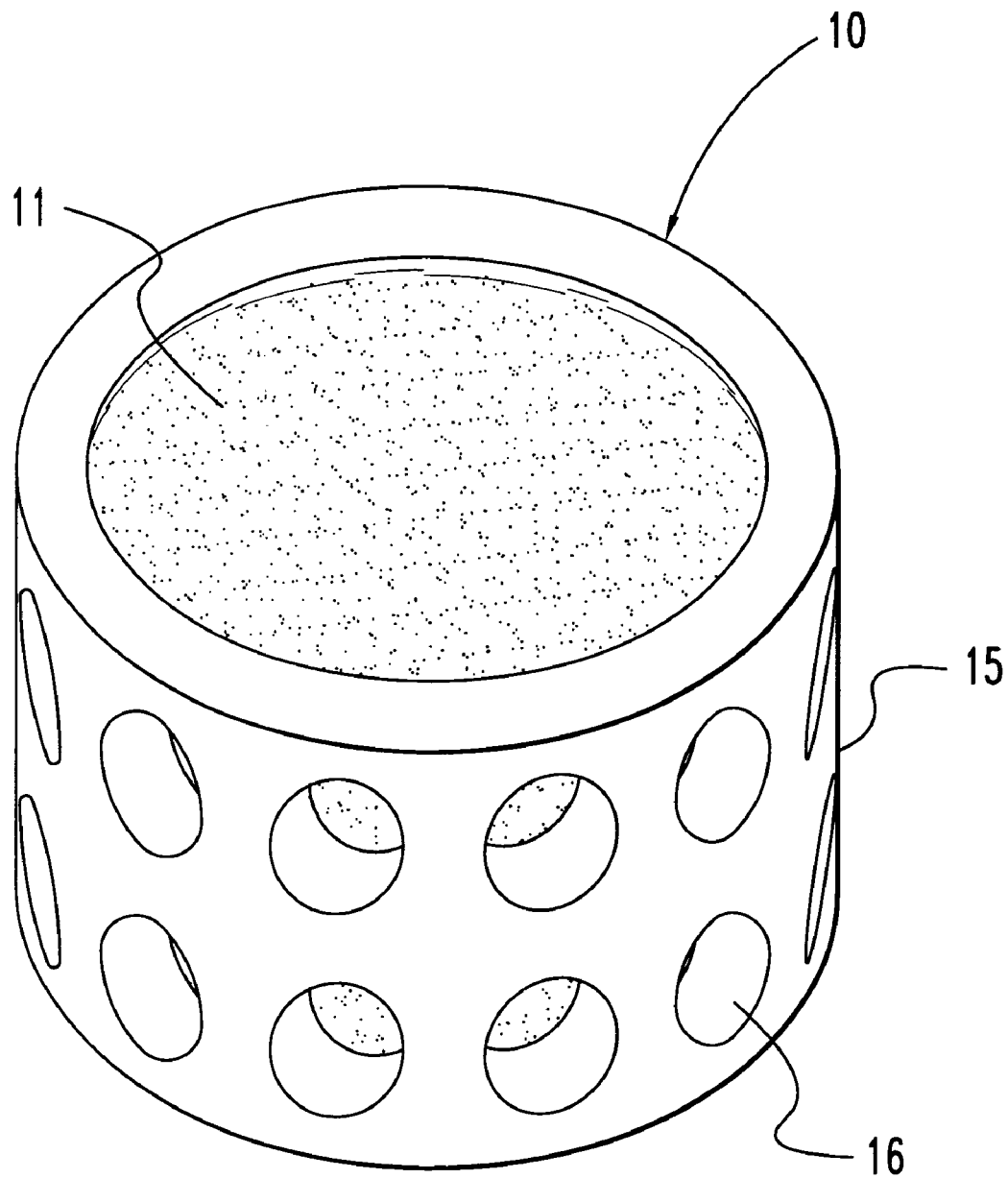
FIG. 1 is a side elevational view of a spinal implant according to one embodiment of this invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention provides spinal implants which include a body composed of a porous biocompatible material reinforced by an outer sleeve made of a second material which is relatively stronger under the compressive load of the spine than the biocompatible material. The inventive implants restore the intervertebral disc space, provide a large surface area for bone ingrowth and eliminate the need for autografts. Implants according to this invention provide immediate load bearing capability and support for the vertebral column without stress shielding the bone implant material. In some aspects, the body is composed of an osteoconductive material including but not limited to bioceramics, autograft, allograft and xenograft. In preferred embodiments, the material is a deactivated bone material in synergistic combination with a bone growth factor such as bone morphogenetic protein (BMP).

Figure 2:
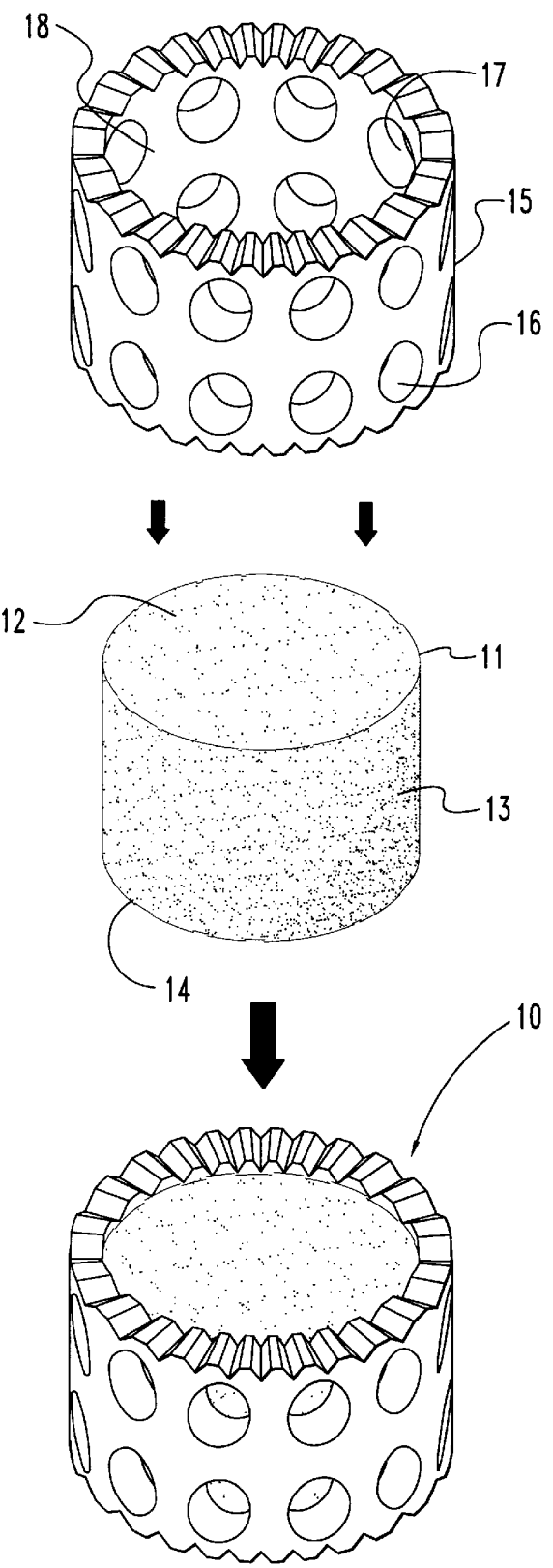
FIG. 2 is an exploded view of the implant of FIG. 1

A spinal implant 10 for engagement between vertebrae in accordance with a preferred embodiment of the present invention is depicted in FIGS. 1 and 2. The implant 10 includes a body 11 composed of a porous biocompatible material for permitting tissue ingrowth therethrough. The body 11 includes two opposite faces 12, 14 and an outer surface 13 disposed between the two faces 12, 14. The body 11 is sized and configured for engagement between two vertebrae V, as shown in FIGS. 3 and 4.

Figure 3:
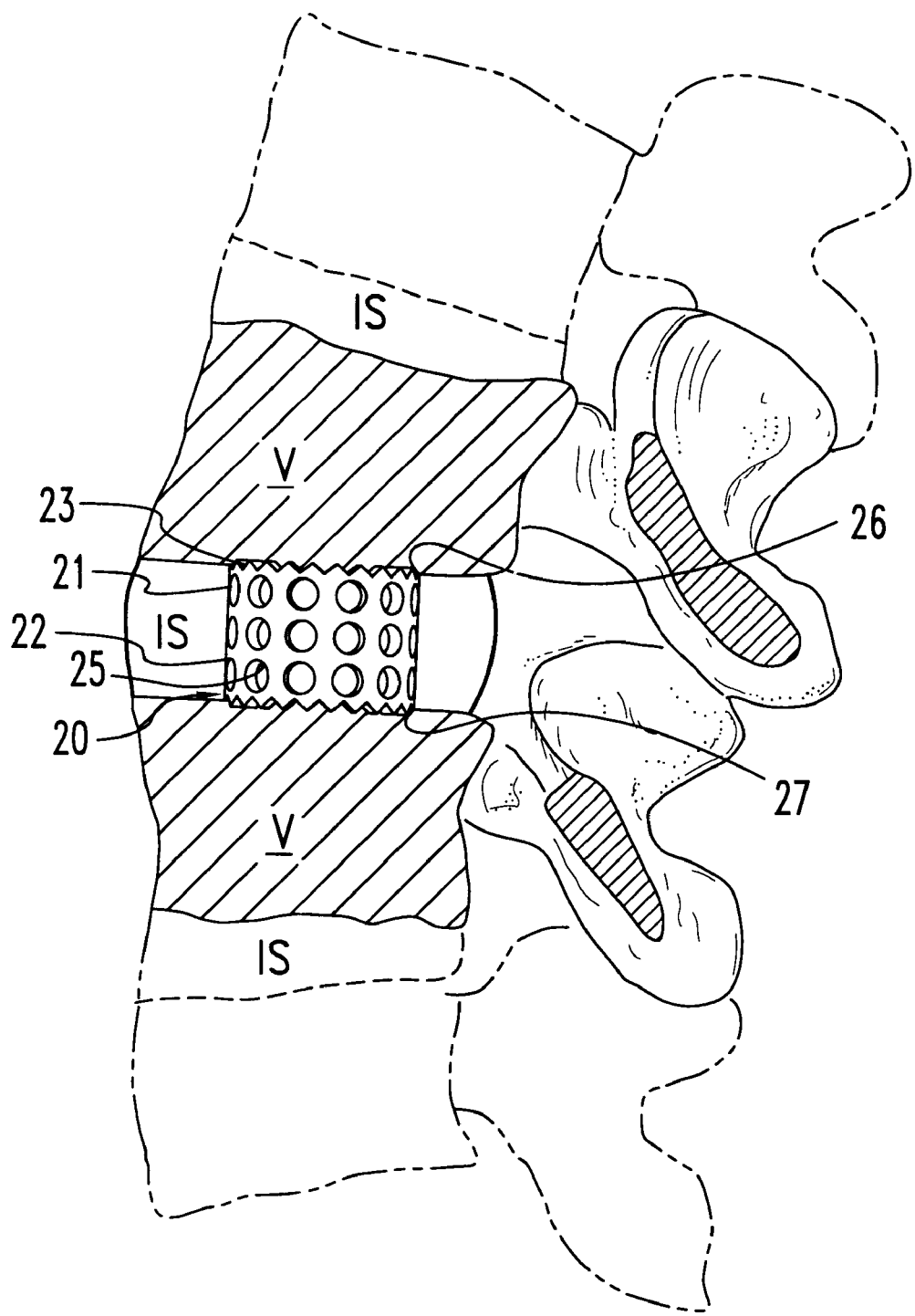
FIG. 3 is a partial side sectional view of a spinal column having an implanted cylindrical interbody fusion device.
Figure 5:
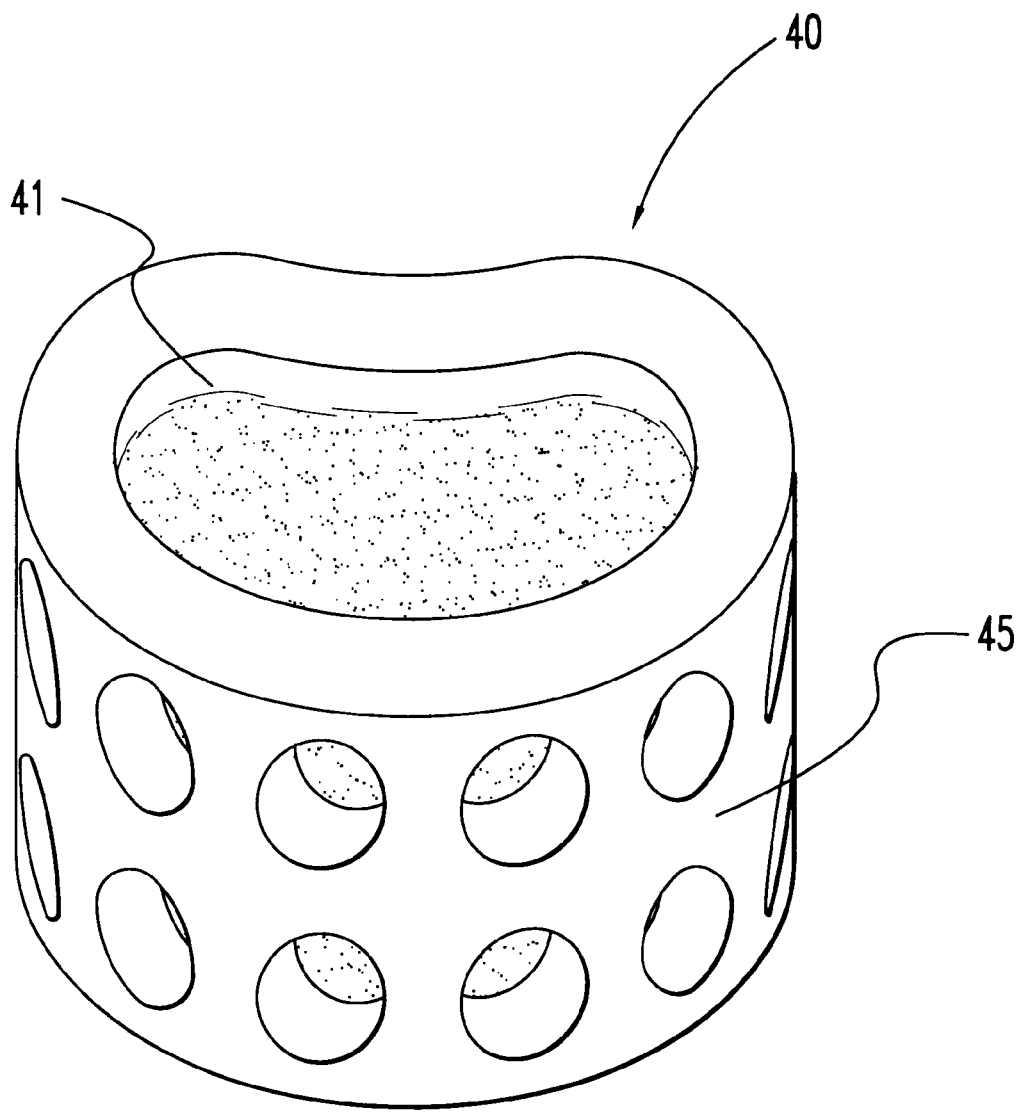

FIG. 3 shows an interbody fusion device 20 according to this invention engaged within the intervertebral space IS between two vertebrae V. Preferably, the body 25 has a height approximating the height of a human disc space IS, and the opposite faces 26, 27 of the body each have a size and shape corresponding to the endplates of each of the vertebrae V. As shown in FIG. 5, the body 41 may have a kidney-shaped cross-section which approximates the size and shape of a nucleus pulposus which has been removed from an intervertebral disc, or the complete disc or vertebral endplate. In the embodiment shown in FIG. 3, the body is preferably sized and shaped to fit snugly within the space IS defined by the endplates and annuli of the adjacent vertebral bodies V. An alternate shape for the body is shown in FIGS. 6 and 7. In some applications, it may be preferable that the height of the body 25 be slightly larger than the height of a human disc space IS to preserve disc space height under the compressive forces of the spine and to avoid the effects of boney erosion.

Figure 4:
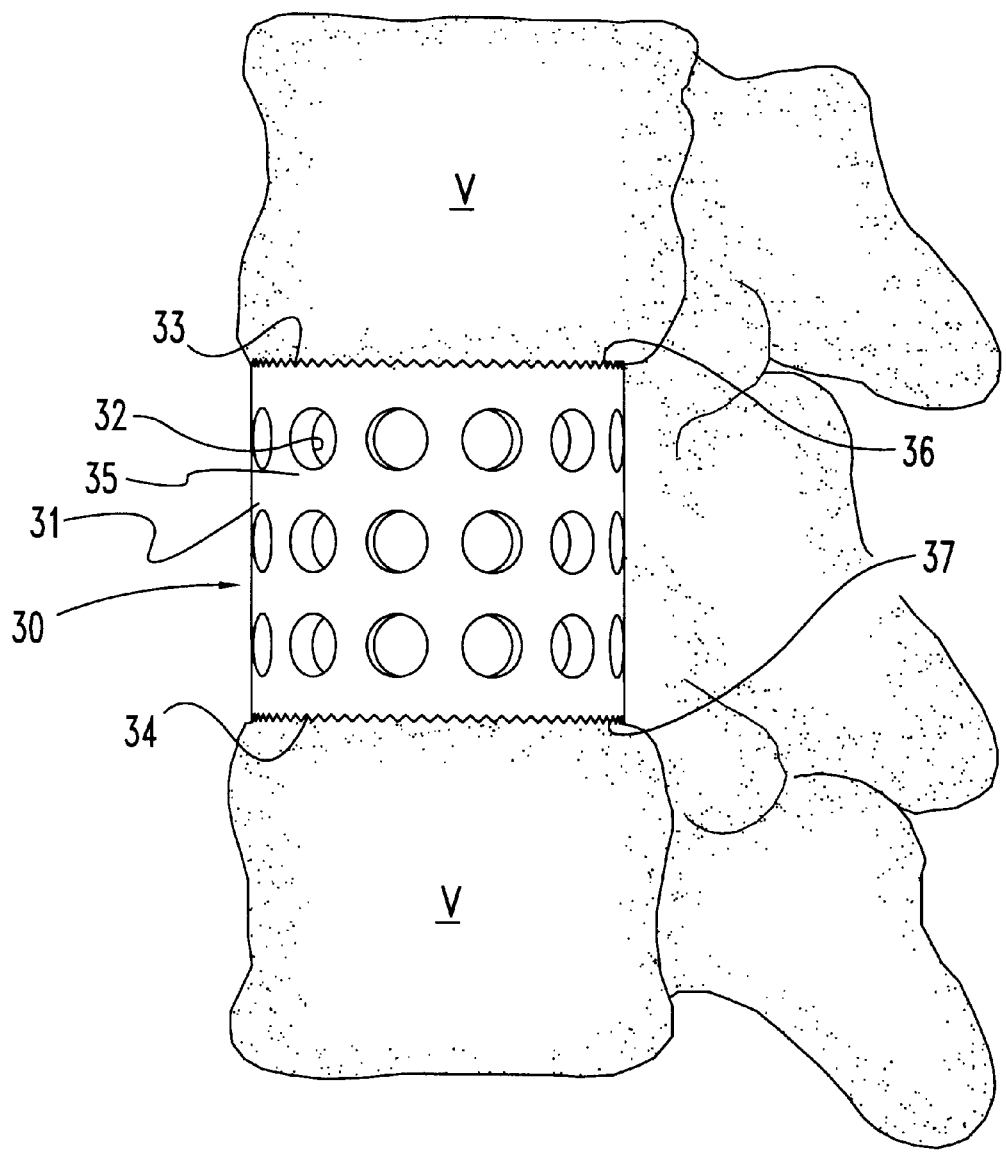
FIG. 4 is a partial side elevational view of a spinal column having an implanted cylindrical vertebral body replacement device.

The invention also contemplates vertebral body replacement devices 30 for use in restoring the space left by the removal of a defective spinal element located between adjoining healthy vertebral bodies V as shown in FIG. 4. In such cases, the body 35 is configured to be locatable within the space between the adjoining vertebral bodies V. The invention contemplates that the body 35 may be any shape or size which is desirable for a spinal implant for engagement between vertebrae V.

The body is composed of a porous biocompatible material for encouraging bone ingrowth. Any porous biocompatible material is contemplated. Such materials and methods of preparing them are well known in the art. Bioceramics are preferred because they exhibit bioactive osteoconductivity.

Calcium phosphate ceramics such as hydroxyapatite, tricalcium phosphate, tetracalcium phosphate, α calcium pyrophosphate, β calcium pyrophosphate and mixtures thereof are preferred. It is contemplated that the biocompatible material may include collagen-ceramic composites as described in Toth, 1993 or ceramic-growth factor composites. Preferably, the ceramic-growth factor composite would be a ceramic-bone morphogenic protein (BMP) composite. BMP can be delivered to the fusion site via pores of the ceramic.

Biphasic calcium phosphate composites are preferred for optimal bone ingrowth and strength and may be prepared according to methods known in the art. (Dilecrin, 1992; Yubaoi 1993; Xingdong, 1993). The biphasic composites may include from about 10% to about 90% hydroxyapatite and about 90% to about 10% by weight of a resorbable calcium phosphate. Hydroxyapatite/β-tricalcium phosphate (HA/TCP) biphasic osteoconductive ceramics are particularly preferred as described in U. S. Pat. No. 5,306,303 to Lynch. This biphasic ceramic is biomechanically superior to the human tricortical iliac crest under compressive loading. Fusion rates with this ceramic with porosities of 30%, 50% and 70% have been found to be superior to the iliac crest autograft in a goat model. (An et al., 1995).

The ratio of HA/TCP affects the rate of biodegradability. Hydroxyapatite provides strength but it is slowly degraded. β-tricalcium phosphate is relatively weak and rapidly degraded. HA/TCP biphasic ceramics may include from about 10% to about 90% hydroxyapatite and from about 90% to about 10% tricalcium phosphate by weight. The ceramic may include 60% hydroxyapatite and 40% tricalcium phosphate by weight, but most preferably, the ceramic will include 50% hydroxyapatite and 50% tricalcium phosphate by weight.

Porosity of the biocompatible material is required for ingrowth, but it is generally understood that as porosity increases, strength decreases. Implants according to the present invention will optimize porosity with strength requirements to avoid fracture. The biocompatible materials of this invention preferably include porosities of between about 40% and about 60%, with a 50% porosity being most preferred. A pore diameter of at least 200 to 600 microns is required for bone ingrowth. Therefore, the ceramics of the present invention are contemplated to have a mean pore size of about 200 to about 700 microns. Preferably, the mean pore size is about 400 microns.

Referring again to FIGS. 1 and 2, a spinal implant 10 according to this invention includes a sleeve 15 disposed around the outer surface 13 of the body 11. The sleeve 15 is composed of a second material which is relatively stronger under compressive loads than the porous biocompatible material. Preferably, the second material is composed of a metal material. The metal material includes any surgically suitable metal including titanium, titanium-vanadium-aluminum alloy, cobalt-chromium alloy, cobalt-chromium-molybdenum alloy, cobalt-nickel-chromium-molybdenum alloy, biocompatible stainless steel, tantalum, niobium, hafnium, tungsten and alloys thereof. Preferably, the metal is 316 LVM stainless steel, titanium or tantalum foam. Most preferably, the metal material is an open-cell tantalum foam as described in U.S. Pat. No. 5,282,861 to Kaplan. This material is a carbon-metal composite including a skeleton of vitreous carbon defining a network of interconnecting pores which are infiltrated with tantalum or another suitable metal by chemical vapor deposition. This material is advantageous because it provides the strength of other metals to serve as a scaffold and prosthesis but also mimics the structure of bone. The interconnecting pores of the foam serve as another site for bone ingrowth. According to the present invention, a disc of tantalum foam can be prepared according to the Kaplan patent. The center of the tantalum foam disc can then be drilled out to obtain a metal foam sleeve. The implant 50 which is depicted in FIG. 12 can be made from the metal foam sleeve 51 and a suitable body 52.

Referring to FIG. 2, the sleeve 15 includes an inner surface 17 for contacting the outer surface 13 of the body 11. The inner surface 17 of the sleeve 15 defines a chamber 18. Preferably, the sleeve 15 is formed of a temperature responsive material, such as a metal, such that the chamber 18 has a first inner dimension that is slightly larger than an outer dimension of the body 11 when the sleeve 15 is in a heated state. In this state, the sleeve 15 can slidably receive the body 11 therein. The chamber 18 has a second inner dimension that is slightly smaller than the body 11 when the sleeve 15 is in a cooled state to thereby clamp the body 11 therein. In other words, the sleeve 15 can be expanded by the application of heat and then shrunk around the body 11 by cooling. Alternatively, when the body 11 is a ceramic, it can be formed within the chamber 18 of the sleeve 15.

The size and shape of the sleeve 15 corresponds to the configuration of the outer surface 13 of the body 11 as shown in FIGS. 2 and 5–11. For example, when the body is cylindrical, the sleeve is a hollow cylinder as shown in FIGS. 6–11. In one specific embodiment of the invention, the sleeve 15 has a height which is less than a height of the outer surface 13 of the body 11 to permit contact of the opposite faces 12, 14 of the body 11 with endplates of the corresponding vertebrae V when the implant is implanted between the vertebrae V.

Referring to FIG. 1, an implant according to the present invention preferably includes a sleeve 15 which defines a plurality of apertures 16 defined therethrough in communication with the outer surface 13 of the body 11 for bone ingrowth. Any suitable shape is contemplated for the apertures. As shown in FIGS. 6–11, the apertures may be generally circular, oval, diamond shaped or rectangular. However, the size and number of apertures must be controlled to maintain the overall strength of the sleeve 15.

Preferably, the implants of the present invention include attaching means for attaching the sleeve 21, 31 of the implants to the adjoining vertebral bodies V as shown in FIGS. 3 and 4. In one specific embodiment depicted in FIG. 3, the attaching means includes teeth 23 disposed at the superior 26 and inferior 27 ends of the sleeve 21. As shown in FIG. 4, the attaching means may alternatively include roughened surfaces 33, 34 defined on the superior 36 and inferior 37 ends of the sleeve 31. The roughened surfaces can be formed by conventional machining techniques, such as knurling.

In one embodiment, shown in FIG. 13, the sleeve 56 includes stops 57, 58, which contact the adjacent vertebral bodies to prevent the device 55 from slipping forward within the disc space.

In a preferred embodiment, the body 11 of the spacer 10 is shaped from bone. The combination of the reinforcing sleeve 15 and the body 11 composed of a bone material provides a load bearing bone graft. It is contemplated that any suitable bone material may be used. The bone material may be autogeneic, allogeneic or xenogeneic. For example, the bone grafts of copending application, Ser. No. 08/740, 031 can be combined with the reinforcement sleeve of the present invention to provide a reinforced bone graft having a high compressive strength. The text of that application is hereby incorporated by reference.

In one preferred embodiment, the bone material is deactivated, i.e., is treated to remove fat and protein. The deactivated bone material may be, for example, as described in U.S. Pat. No. 5,417,975 to Lussi et al., U.S. Pat. No. 4,314,380 to Miyata et al., U.S. Pat. No. 5,573,771 to Geistlich et al., U.S. Pat. No. 4,882,149 to Spector, "A Chemosterilized Antigen-Extracted Autodigested Alloimplant for Bone Banks" by Urist MD, et al., in Arch Surg/Vol. 110, April 1975 and "Xenogeneic Bone Grafting in Humans by Salama, in *Xenogeneic Bone Grafting,* Number 174, April 1983. In some of these methods, the deactivated bone material has been treated to remove all of the bone proteins which results in a powdery mineral material. In such cases, it is important to add collagen, gelatin or a similar protein or composition to provide the correct consistency.

Most preferably, the deactivated bone material will be a selectively deactivated bone material which is described in copending application, Ser. No. 08/873,276, filed Jun. 11, 1997 or is available from the University of Florida Tissue Bank, Inc. (UFTB) 1 Innovation Drive, Alachua, Fla. 32615, 904-462-3097 or 1-800-OAGRAFT. This material has been treated to remove all of the non-collagenous bone proteins leaving a non-immunogeneic disease-free bone product. This product has the natural chemistry and mineral microcrystalline structure of bone with a consistency which can be shaped into desired forms.

The selectivly deactivated product is preferred because it has a micro-structure which is the closest to natural bone of all of the known treated bone products. This bone product also has the radiopacity of natural bone and does not show the dense white image of the bone mineral of Spector. The selectively deactivated product also provides superior resorbability, particularly when combined with an osteogenic factor. Resorption has been found to advantageously occur within several months as opposed to several years of the Spector material or the few weeks of the Urist product. When the material is combined with a bone growth factor, the resorption time is ample for forming the boney bridge required for fusion and bone healing. The selectively deactivated material also has an elasticity similar to normal bone while the Spector and Geistlich materials have been found to be brittle and weak.

The bone materials of this invention are preferably synergistically combined with an osteogenic composition or material containing a bone growth factor or protein. An osteogenic material can be applied to the bone material by impregnating the graft with a solution including an osteogenic composition. The composition may be applied by the surgeon during surgery or the spacer may be supplied with the composition preapplied. In such cases, the osteogenic composition may be stabilized for transport and storage such as by freeze-drying. The stabilized composition can be rehydrated and/or reactivated with a sterile fluid such as saline or water or with body fluids applied before or after implantation. The term osteogenic composition used here means virtually any material that promotes bone growth or healing including natural, synthetic and recombinant proteins, hormones and the like.

The osteogenic compositions used in this invention preferably comprise a therapeutically effective amount to stimulate or induce bone growth or healing of a substantially pure bone inductive factor such as a bone morphogenetic protein in a pharmaceutically acceptable carrier. The preferred osteoinductive factors are the recombinant human bone morphogenic proteins (rhBMPs) because they are available in unlimited supply and do not transmit infectious diseases. Most preferably, the bone morphogenetic protein is a rhBMP-2, rhBMP-4 or heterodimers thereof. The concentration of rhBMP-2 is generally between about 0.4 mg/ml to about 1.5 mg/ml, preferably near 1.5 mg/ml. However, any bone morphogenetic protein is contemplated including bone morphogenetic proteins designated as BMP-1 through BMP-13. BMPs are available from Genetics Institute, Inc., Cambridge, Mass. and may also be prepared by one skilled in the art as described in U.S. Pat. Nos. 5,187,076 to Wozney et al.; U.S. Pat No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent No. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenic protein from bone are described in U.S. Pat. No. 4,294,753 to Urist and Urist et al., 81 PNAS 371, 1984.

The choice of carrier material for the osteogenic composition is based on biocompatibility, biodegradability, and interface properties. The bone growth inducing composition can be introduced into the pores of the bone material in any suitable manner. For example, the composition may be injected into the pores of the graft. In other embodiments, the composition is dripped onto the graft or the graft is soaked in a solution containing an effective amount of the composition to stimulate osteoinduction. In either case the pores are exposed to the composition for a period of time sufficient to allow the liquid to throughly soak the graft. The osteogenic factor, preferably a BMP, may be provided in freeze-dried form and reconstituted in a pharmaceutically acceptable liquid or gel carrier such as sterile water, physiological saline or any other suitable carrier. The carrier may be any suitable medium capable of delivering the proteins to the spacer. Preferably the medium is supplemented with a buffer solution as is known in the art. In one specific embodiment of the invention, rhBMP-2 is suspended or admixed in a carrier, such as water, saline, liquid collagen or injectable bicalcium phosphate. The BMP solution can be dripped into the graft or the graft can be immersed in a suitable quantity of the liquid. In a most preferred embodiment, BMP is applied to the pores of the graft and then lypholized or freeze-dried. The graft-BMP composition can then be frozen for storage and transport.

In a specific embodiment for use in the cervical spine, the body has a height of 8 mm and a diameter of 11 mm. The sleeve has an overall height of 10 mm, including teeth, and a height of slightly over 8 mm between the teeth. The sleeve in the specific embodiment has an inner diameter slightly less than 11 mm and a wall thickness of about 1 mm. The sleeve is provided with twenty-four uniformly sized and spaced apertures having a diameter of about 2 mm.

The implants and spacers of this invention may be implanted according to surgical procedures which are well known in the art. In addition, the implants and spacers can be implanted following a full or partial discectomy of the instrumented disc space.

Implants and spacers according to the present invention have compressive strengths sufficient to withstand the normal loads on the spinal column. These inventive implants and spacers are at least as strong as tricortical iliac crest grafts. The implants and spacers have an ASTM C-773 compressive strength of at least 7 MPa, preferably at least 20 MPa and most preferably at least 40 MPa. Under these loads, the outer sleeve will bear most of the load without bending or fracture, to protect the more brittle and weaker ceramic material within.

Implants according to this invention combine the advantages of porous biocompatible materials with stronger materials such as metals. The implants provide immediate load bearing capability without stress shielding. The sleeve composed of the stronger materials provides a tension band around the porous biocompatible material to prevent fracture of the body. The body carries the initial load and slowly transfers it to the newly formed bone. The porous biocompatible material provides a large surface area for bone ingrowth and eliminates the needs for autograft. Where the biocompatible material is a bioceramic or a bone graft, it will be eventually resorbed and replaced by host bone.

The use of a deactivated bone body in synergistic combination with a bone growth factor in this invention solves many of the problems of using bone graft. The deactivation process removes immunogenic and disease causing agents while retaining the natural microstructure of bone. This advantageously allows the use of xenograft, which is available in virtually unlimited supply. Fortifying the graft with a bone growth factor yields an osteoinductive graft which makes the pain and risk of harvesting autograft unnecessary. The combination of a bone material with a reinforcement member provides a load bearing graft which avoids the disadvantages of a metal implant, such as stress shielding. Therefore, this invention combines all of the advantages of autograft, allograft, xenograft and metal spacers without any of the corresponding disadvantages.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

REFERENCES

The following references are indicative of the level of skill in the art and are hereby incorporated by reference in their entirety as if each had been individually incorporated by reference and fully set forth.

An et al., Porous Biphasic Ceramics for Cervical Fusion, *Spine*, accepted for publication, 1995.

Delecrin et al., Biphasic Calcium Phosphate as a Bone Graft Substitute for Spine Fusion: Stiffness Evaluation, *Fourth World Biomaterials Congress*, 1992 (p. 644).

Li Yubaoi et al., The Influence of Multiphase Calcium Phosphate Bioceramics on Bone Formation in Nonosseous Tissues, *Society for Biomaterials*, 1993 (p. 165).

Toth et al., Ceramic-induced Osteogenesis Following Subcutaneous Implantation of Calcium Phosphates, *Bioceramics*, Vol. 6 eds. Ducheyne & Christianson, 1993 (pp. 9–14).

Toth et al., Comparison of Compressive Strengths of Iliac Bone Grafts and Porous Calcium Phosphate Ceramics for Spine Fusion, *Orthopaedic Research Society*, 1994 (p. 719).

Xingdong et al., Initiation of the Osteoinduction in Calcium Phosphate Ceramics with the Bone Growth Factor, *Society for Biomaterials*, 1993 (p. 299).

U.S. Pat. No. 5,282,861 to Kaplan.
U.S. Pat. No. 5,417,975 to Lussi et al.
U.S. Pat. No. 4,314,380 to Miyata et al.
U.S. Pat. No. 5,573,771 to Geistlich et al.
U.S. Pat. No. 4,882,149 to Spector.

A Chemosterilized Antigen-Extracted Autodigested Alloimplant for Bone Banks by Urist MD, et al., in Arch Surg/Vol. 110, April 1975

Xenogeneic Bone Grafting in Humans by Salama, in Xenogeneic Bone Grafting, Number 174, April 1983.

What is claimed:

1. An interbody fusion spacer, comprising:
    a body having an outer surface and a height approximating the height of a human disc space, said body composed of a porous, biocompatible ceramic material for permitting tissue ingrowth therethrough; and
    a reinforcing sleeve disposed around said outer surface of said body, said sleeve including a material relatively stronger under compression than said porous, biocompatible ceramic material; and
    said reinforcing sleeve having an inner surface defining a chamber, said chamber having an inner dimension that is slightly smaller than said body so as to engage said sleeve to said body.

2. The spacer of claim 1 wherein said sleeve defines a plurality of apertures therethrough in communication with said outer surface of said body for bone ingrowth.

3. The spacer of claim 2 wherein said apertures are generally circular.

4. The spacer of claim 2 wherein said apertures are generally oval.

5. The spacer of claim 2 wherein said apertures are generally diamond-shaped.

6. The spacer of claim 2 wherein said apertures are generally rectangular.

7. The spacer of claim 1 wherein:
    said sleeve includes an inner surface for contacting said outer surface of said body, said inner surface of said sleeve defining a chamber;
    said sleeve being formed of a temperature responsive material such that said chamber has a first inner dimension that is slightly larger than an outer dimension of said body when said sleeve is in a heated state to slidably receive said body therein; and
    said chamber has a second inner dimension that is slightly smaller than said body when said sleeve is in a cooled state to thereby clamp said body therein.

8. The spacer of claim 1 wherein said sleeve has a height less than a height of said outer surface to permit contact of said opposite faces with endplates of the corresponding vertebrae when the spacer is implanted between the vertebrae.

9. The spacer of claim 1, further comprising: attaching means for attaching said sleeve to the endplates of the adjacent vertebral bodies.

10. The spacer of claim 9 wherein:
    said sleeve includes an inferior end and a superior end; and
    said attaching means includes teeth disposed at said superior end and said inferior end of said sleeve.

11. The spacer of claim 9 wherein:
    said sleeve includes an inferior end and a superior end; and
    said attaching means includes roughened surfaces defined on said superior end and said inferior end of said sleeve.

12. The spacer of claim 1 wherein said body is cylindrical and said sleeve is a hollow cylinder.

13. The spacer of claim 1 wherein said opposite faces of said body each have a size and shape corresponding to the shape of a vertebral endplate.

14. The spacer of claim 1 wherein said sleeve has an outer shape approximating the shape of a vertebral endplate.

15. The spacer of claim 1 wherein said sleeve is composed of a metal material.

16. The spacer of claim 15 wherein said metal material includes a metal selected from the group consisting of tantalum, niobium, hafnium, tungsten and alloys thereof.

17. The spacer of claim 15 wherein said metal material is a tantalum foam.

18. The spacer of claim 15 wherein said sleeve is composed of a metal material including a metal selected from the group consisting of titanium, titanium-vanadium-aluminum alloy, cobalt-chromium alloy, cobalt-chromium-molybdenum alloy, cobalt-nickel-chromium-molybdenum alloy and biocompatible stainless steel.

19. The spacer of claim 18 wherein said biocompatible stainless steel is 316 LVM stainless steel.

20. The spacer of claim 15 wherein said metal material includes titanium.

21. The spacer of claim 1 wherein said spacer has an ASTM C-773 compressive strength of at least 7.1 MPa.

22. The spacer of claim 20 wherein said spacer has a compressive strength of at least 20 MPa.

23. The spacer of claim 21 wherein said spacer has a compressive strength of at least 40 MPa.

24. The spacer of claim 1 wherein said body has a kidney-shaped cross-section to conform to the shape of vertebral endplates.

25. The spacer of claim 1 wherein said body is configured to approximate a size and shape of a nucleus pulposus of a natural intervertebral disc.

26. The spacer of claim 1 wherein said ceramic material is a calcium phosphate ceramic.

27. The spacer of claim 1 wherein said ceramic material is a biphasic calcium phosphate ceramic.

28. An interbody fusion device, comprising:

a body having an outer surface and a height approximating the height of a human disc space, said body including a porous, biocompatible, biodegradable material for permitting tissue ingrowth therethrough; and a sleeve engaged to said outer surface of said body, said sleeve including a material relatively stronger under compressive loads than said biocompatible material and including an inner surface for contacting said outer surface of said body, said inner surface of said sleeve defining a chamber, said sleeve being formed of a temperature responsive material such that said chamber has a first inner dimension that is slightly larger than an outer dimension of said body when said sleeve is in a heated state to slidably receive said body therein, and said chamber having a second inner dimension that is slightly smaller than said body when said sleeve is in a cooled state to thereby clamp said body therein.

29. An interbody fusion spacer, comprising:

a body having an outer surface and a height approximating the height of a human disc space, said body composed of a porous, biocompatible material for permitting tissue ingrowth therethrough; and a reinforcing sleeve clamped around said outer surface of said body, said sleeve including a material relatively stronger under compression than said porous, biocompatible material.

30. The spacer of claim 29, further comprising a therapeutically effective amount to stimulate bone growth of a bone growth factor dispersed within said body.

31. The spacer of claim 29 wherein said sleeve defines a plurality of apertures therethrough in communication with said outer surface of said body for bone ingrowth.

32. A spinal implant for engagement between vertebrae, comprising:

a monolithic body having two opposite faces and an outer surface disposed between said two faces, said body including a porous, biocompatible material for permitting tissue ingrowth therethrough, said body being sized and configured for engagement between two vertebrae;

a sleeve disposed around said outer surface of said body, said sleeve including a second material relatively stronger under compressive loads than said porous, biocompatible material;

said sleeve including an inner surface for contacting said outer surface of said body, said inner surface of said sleeve defining a chamber; and said chamber having an inner dimension that is slightly smaller than said body so as to engage said sleeve to said body.

33. The spacer of claim 29, wherein said body is composed of bone.

34. The spacer of claim 29, wherein said porous, biocompatible material comprises biocompatible ceramic.

35. The spacer of claim 33, wherein said bone has been processed to remove associated non-collagenous bone proteins, said bone containing native collagen materials and naturally associated bone minerals and substantially free from non-collagenous protein.

36. An interbody fusion spacer, comprising:

a body having an outer surface and a height approximating the height of a human disc space, said body composed of a porous, biocompatible ceramic material for permitting tissue ingrowth therethrough; and a reinforcing sleeve engaged to said outer surface of said body, said sleeve including a material relatively stronger under compression than said porous, biocompatible ceramic material;

said sleeve including an inner surface for contacting said outer surface of said body, said inner surface of said sleeve defining a chamber;

said sleeve being formed of a temperature responsive material such that said chamber has a first inner dimension that is slightly larger than an outer dimension of said body when said sleeve is in a heated state to slidably receive said body therein; and said chamber having a second inner dimension that is slightly smaller than said body when said sleeve is in a cooled state to thereby clamp said body therein.

* * * * *